United States Patent
Leal (10) Patent No.: US 11,974,548 B2
(45) Date of Patent: May 7, 2024

(54) METHODS OF VENTRAL RECEPTACLE COMPRESSION TECHNIQUE FOR SCORING MATED STATUS IN INSECTS INCLUDING FRUIT FLIES

(71) Applicant: THE UNITED STATES OF AMERICA, AS REPRESENTED BY THE SECRETARY OF AGRICULTURE, Washington, DC (US)

(72) Inventor: Sandra N. Leal, Harlingen, TX (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 923 days.

(21) Appl. No.: 16/991,522

(22) Filed: Aug. 12, 2020

(65) Prior Publication Data

US 2021/0045363 A1    Feb. 18, 2021

Related U.S. Application Data (60) Provisional application No. 62/885,401, filed on Aug. 12, 2019.

(51) Int. Cl.
    *A61D 19/00*      (2006.01)
    *A01K 29/00*      (2006.01)
    *A01K 67/033*     (2006.01)

(52) U.S. Cl.
    CPC .......... *A01K 29/005* (2013.01); *A01K 67/033* (2013.01); *A61D 19/00* (2013.01)

(58) Field of Classification Search
None
See application file for complete search history.

(56) References Cited

PUBLICATIONS

Twig et al. Function of multiple sperm storage organs in female Mediterranean fruit flies (*Ceratitis capitata*, Diptera: Tephritidae) (2005), Journal of Insect Physiology, 51, pp. 67-74. (Year: 2005).*
Harmer et al. Remating inhibition in female Queensland fruit flies: Effects and correlates of sperm storage (2006), Journal of Insect Physiology, 52, pp. 179-186. (Year: 2006).*
Thomas et al. Sperm Depletion in Singly Mated Females of the Mexican Fruit Fly (Diptera:Tephritidae) (Jan. 2018), Journal of Entomological Science, 53, pp. 82-88. (Year: 2018).*
Thomas et al. Copula Duration, Insemination, and Sperm Allocation in Anastrepha ludens (Diptera: Tephritidae) (2014) Annals of the Entomological Society of America, 107, pp. 858-865. (Year: 2014).*
Fritz et al. Sperm Storage Patterns in Singly Mated Females of the Caribbean Fruit Fly, *Anastrepha suspensa* (Diptera: Tephritidae) (2004), Annals of the Entomological Society of America, 97, pp. 1328-1335. (Year: 2004).*

* cited by examiner

*Primary Examiner* — Kara D Johnson
*Assistant Examiner* — Maytee Marie Contes De Jesus
(74) *Attorney, Agent, or Firm* — Nath, Goldberg & Meyer; Joshua B. Goldberg (57) ABSTRACT

A method for determining the mated status of female fruit flies, focusing on determining the presence of spermatozoa in a sample fly's ventral receptacle (VR). The ventral receptacle is the organ where eggs become fertilized. The VR is the first and last organ in a mated female fly to contain spermatozoa. The VR is thus the most accurate organ for determining whether a female fruit fly has recently mated. The method is a squash method. The fly's ventral receptacle is isolated, and then squeezed so as to cause spermatozoa stored in the ventral receptacle to be released into the lumen of the VR. This permits use of a microscope to determine the presence or absence of spermatozoa in the female fruit fly, and thus the mated status of the female fruit fly.

19 Claims, 11 Drawing Sheets

METHODS OF VENTRAL RECEPTACLE COMPRESSION TECHNIQUE FOR SCORING MATED STATUS IN INSECTS INCLUDING FRUIT FLIES

BACKGROUND

Fruit flies generally include two fly families—*Tephritidae*, and *Drosophilidae* (often called the "common fruit fly"). There are nearly 5,000 known species of tephritid fruit flies, in almost 500 genera of the *Tephritidae* family. Among the *Tephritidae* family, the genus *Anastrepha* is the most diverse genus in much of the Americas. This genus includes more than 300 known species, including the Mexican fruit fly, the South American fruit fly, the West Indian fruit fly, the sapote fruit fly, the Caribbean fruit fly, the American guava fruit fly, the pumpkin fruit fly, and the papaya fruit fly.

Fruit flies are often attracted to fresh and rotting fruit, as well as various parts of certain plants. Females deposit eggs in living, healthy plant tissue—including unripe fruit. Upon emerging from the eggs, the larvae feed on the ripening or rotting fruit, or various parts of the plants. Fruit flies can present a nuisance in the home or garden—affecting both growing plants and fruit, as well as ripe fruit brought into the house.

However, agriculturally, fruit flies can present major ecologic and economic problems, causing significant damage to fruit and other plant crops. Some fruit flies feed on only one type of plant, while others are less specific. Crops that may be affected include olive plants, tropical fruit, vegetables, nut crops, celery and parsnips, sunflowers, and blueberries.

As a result, there has been a lot of focus on controlling fruit fly infestations. Pest management techniques applied to tephritids have traditionally included use of conventional pesticides. However, due to the deleterious impact of pesticides, the trend has been to move to less impactful, more targeted methods. These methods include, for example, toxic food baits, male annihilation techniques using specific male attractant parapheromones in toxic baits or mass trapping. Other methods include sterile insect techniques. Id.

Sterile insect techniques are methods of biologically controlling insect populations. Typically, large numbers of sterile male insects are released in the desired geographic location. The sterile males compete with wild males to mate with wild females. Of course, any sterile male mating with a female will not produce offspring, thereby reducing the production of eggs.

The goal of such sterile insect techniques is to have a large proportion of the females mate with sterile males, reducing the production of the next generation of insects. However, one important factor is the degree to which the females in a particular population mate with the sterile males, without preferentially mating with wild males or also mating with wild males, thereby avoiding the desired result of mating only with sterile males to one degree or another.

A determination of the mated status in wild female fruit flies can be used to help determine the degree of success or failure of a sterile insect technique to achieve the desired results. These determinations provide information to program managers that may be useful in at least two respects. First, the mated (or unmated) status may be a factor in triggering quarantine restrictions at the detection location. A determination that a threshold proportion of invasive female fruit flies that have mated (or unmated) status may be used to trigger a quarantine, for example. Second, the mated status of female fruit flies can give an indication of the sterile male activity and coverage in the area. If a mature female has not mated, that could indicate a problem with sterile male compatibility, competitiveness, or an insufficient release level of sterile males in the area.

Scoring of mated status of wild female fruit flies in a particular geographic area helps determine whether to institute a quarantine at the examined location. With prior art methods of scoring mated status using the spermathecal squash technique, false negatives occur, for example, when the spermathecae become depleted through the course of egg laying.

For example, one traditional means of scoring mated status is known as the spermathecal squash technique. Spermathecae are sperm storage organs in the female fruit fly reproductive tract. Dissections and slide mount squashes of the spermathecae can determine the presence or absence of spermatozoa. However, this method may produce a significant number of false negatives, i.e., females are scored as unmated when in fact they have mated. These false negatives delay quarantine activities, and allow an invasive fruit fly population to build up before additional trapping, bait sprays and larval surveys are implemented.

An accurate, reliable method of determining mated status in fruit flies would provide important economic and ecological information useful in controlling populations.

SUMMARY

The primary seminal storage organ in females is the ventral receptacle (VR). The spermathecae (three in *Anastrepha* species) receive and store the excess or overflow sperm. Depending on the duration of copulation, all, some, or none of the spermathecae will contain spermatozoa.

Further, the VR is the organ where eggs become fertilized. It is located on the ventral side of the bursa copulatrix where the male ejaculates. Thus, the VR is the first and the last organ in the female to contain spermatozoa and is thus the one organ most likely to have spermatozoa if the fly has mated.

Accordingly, the present method, as described herein, is a new squash method that avoids the need to stain the samples being examined, and that provides increased accuracy in the results achieved. This new technique involves squashing the bursa copulatrix under a microscope slide coverslip, causing sperm stored in the seminal receptacle to be released into the lumen of the VR. As such, the sperm is readily visible without need for staining.

Specifically, the present subject matter relates to a method of determining the mated status of a female fruit fly, comprising detecting for the presence or absence of spermatozoa in the female fruit fly's ventral receptacle, wherein if the spermatozoa is present in the female fruit fly's ventral receptacle, the female fruit fly has a positive mated status.

One embodiment of the present subject matter is a method for determining the mated status of female fruit flies. In one embodiment, this method involves squashing the ventral receptacle of a female fruit fly under a microscope slide coverslip so as to rupture the alveoli in the ventral receptacle, enabling determination of whether spermatozoa had been deposited in the ventral receptacle.

Another embodiment of the present subject matter is a further method for determining the mated status of female fruit flies. This method involves isolating the portion of the bursa copulatrix of a female fruit fly that contains the ventral receptacle, and applying pressure to the bursa copulatrix and ventral receptacle, so as to cause any spermatozoa stored in the seminal receptacle to be released into the lumen of the fly's ventral receptacle, enabling use of a microscope to determine whether spermatozoa had been deposited in the ventral receptacle.

Another embodiment of the present subject matter is an additional method for determining the mated status of female fruit flies. This method involves exposing the bursa copulatrix of a female fruit fly by opening the posterior portion of the ovipositor sheath; excising a portion of the bursa copulatrix containing the ventral receptacle; isolating the ventral receptacle from the bursa copulatrix; and applying pressure to the ventral receptacle so as to rupture the alveoli in the ventral receptacle so as to cause spermatozoa present in the ventral receptacle to spill into the lumen of the ventral receptacle; thereby enabling determination of whether spermatozoa had been deposited in the ventral receptacle by a male fruit fly.

DETAILED DESCRIPTION OF THE PREFERRED EMBODIMENTS

Two methods were compared for scoring mated status relying on the VR. The first method is a prior art method; the second method is disclosed here.

The first method is by application of a nuclear stain (such as Aceto-Orcein) that binds to the sperm packets stored within the alveoli of the seminal receptacle found within the lumen of the VR. This method has been published for use as an adjunct to the spermathecal squash method, and has been validated with *Bactrocera, Ceratitis* and *Anastrepha* species. Thomas, D. B., S. N. Leal & H. E. Conway. 2014. *Copula duration, insemination, and sperm allocation in Anastrepha ludens (Diptera: Tephritidae)*. Ann. Ent. Soc. Am. 107: 858-865.

The present method provides a mechanism for determining the mating status of a female fruit fly, in particular by determining the presence of spermatozoa in a female fruit fly without need to stain the samples being examined, and thereby producing more accurate results than are presently possible. This new technique involves squashing the bursa copulatrix of the female fruit fly, such as under a microscope slide coverslip, causing sperm stored in the seminal receptacle, also known as the Ventral Receptacle, to be released into the lumen of the Ventral Receptacle (VR). As a result, the sperm is readily visible under a microscope, without need for staining. Such sperm analyses, or spermiograms, may be used to analyze qualitative and/or quantitative factors regarding the presence and viability of spermatozoa in the prospective female recipient.

In general, a Spermiogram consists of studying in-vivo/in-vitro spermatozoa directly from the male's testes. The presence of sperm in the female recipient (in this case, the Ventral Receptacle) indicates mated status (positive or negative). The in-vivo study of sperm activity within the female's Ventral Receptacle is used as a QA/QC method to score for the male's ability to successfully transfer an adequate amount of sperm into the female's sperm storage organs post-copula. The study "scores" for post-copulatory Sperm Transfer.

Specifically, the female fruit fly is "scored" to identify the presence or absence of sperm in the female fruit fly. This indicates the adequacy or inadequacy of sperm transfer post-copula, and thus the positive or negative mated status for the female fruit fly. The analysis may also be used to determine the sperm activity of any sperm that is present in the female, indicating whether or not the semen is from a sterile male fruit fly.

The diagnostic testing helps determine the presence, quality, and activity level of sperm that may be present in the female fruit fly, and can be used to determine whether any sperm that is present is from a wild (fertile) male, or a sterile male—one of the male flies released by the SIT program. The diagnoses involve application of up to several proprietary analytical tests.

This method is more accurate than prior art methods, such as the spermathecal squash technique. The spermathecal squash technique resulted in false negatives, especially when the spermathecae become depleted through the course of egg laying. A female fruit fly can have as many as three spermathecae (for example, in *Anastrepha* species). The spermathecae receive and store excess or overflow spermatozoa. Depending on the duration of copulation, all, some, or none of the spermathecae will contain spermatozoa.

In contrast, the instant method focuses on the presence of spermatozoa in the female's ventral receptacle. The VR is the organ where eggs become fertilized. The VR is located on the ventral side of the bursa copulatrix—where the male fruit fly typically ejaculates. Accordingly, the VR is generally the first and last organ in the female fruit fly to contain spermatozoa from a male fruit fly, and thus is the one organ most likely to contain spermatozoa if the female fruit fly has mated.

Figure 4:
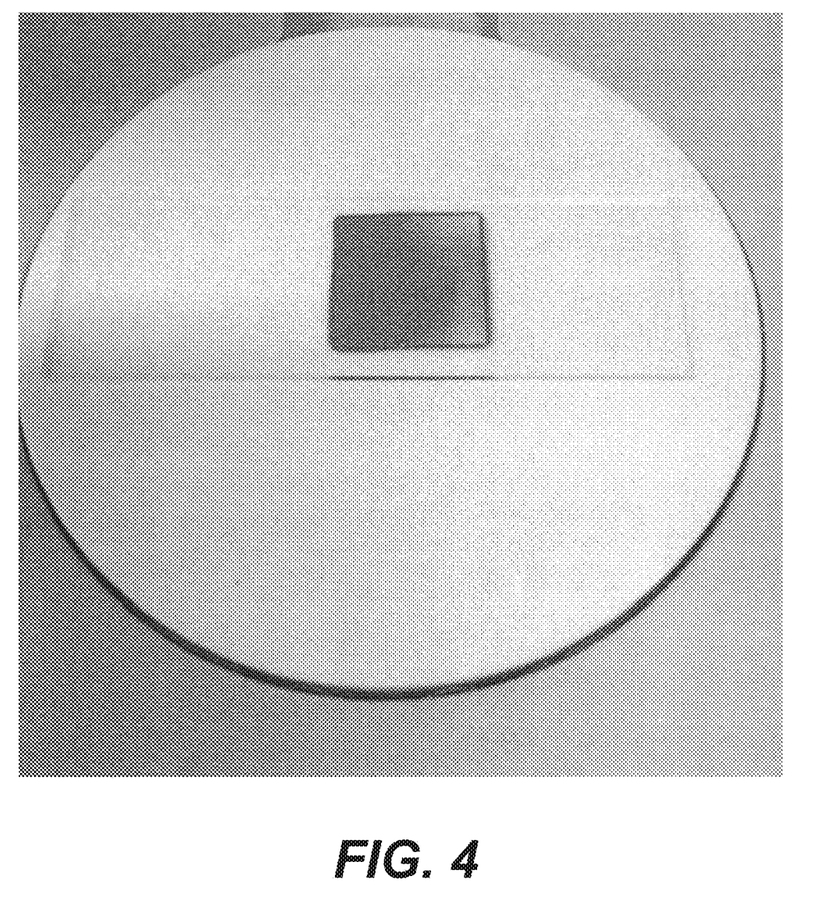
FIG. 4 shows a cover-slip covering the spermathecae, after a drop of Aceto-Orcein stain or saline solution is placed on the spermathecae.
Figure 5:
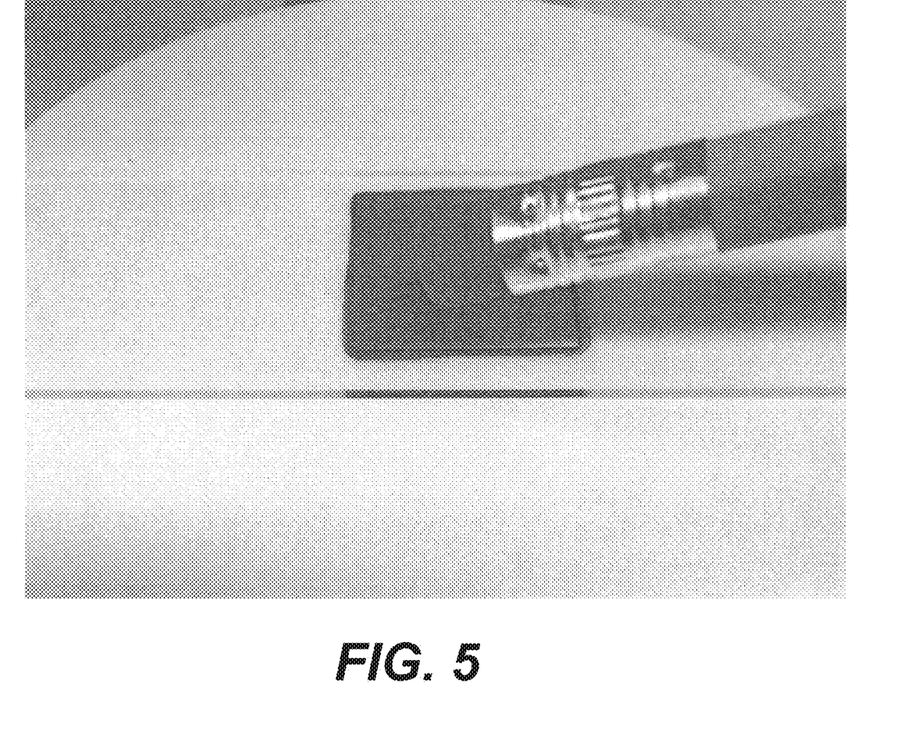
FIG. 5 shows application of gentle gradual pressure on the cover slip covering the spermathecae, using a pencil eraser, to rupture the spermathecae and allow determination of whether spermatozoa are present in the spermathecae.

The prior art spermathecal squash technique method for determining the mating status of a female fruit fly focuses on the sperm packets stored in the spermathecae. This method, depicted in FIGS. 1-5, generally involves cutting open the female fruit fly's abdomen from apex to base (FIGS. 1, 2); dissecting the spermathecae (either one, two, or three) and removing the spermathecae from the female and placing the spermathecae on a microscope slide (FIGS. 3A, 3B, 3C, 3D); placing a drop of Aceto-Orcein stain or saline solution on the spermathecae, and covering the spermathecae with a slide cover-slip (FIG. 4); and applying gentle, gradual pressure on the cover-slip to squeeze the spermathecae, rupturing the spermathecae and allowing evaluation under microscope to determine the presence and activity, or the absence, of spermatozoa from the ruptured spermathecae (FIG. 5).

Figure 8:
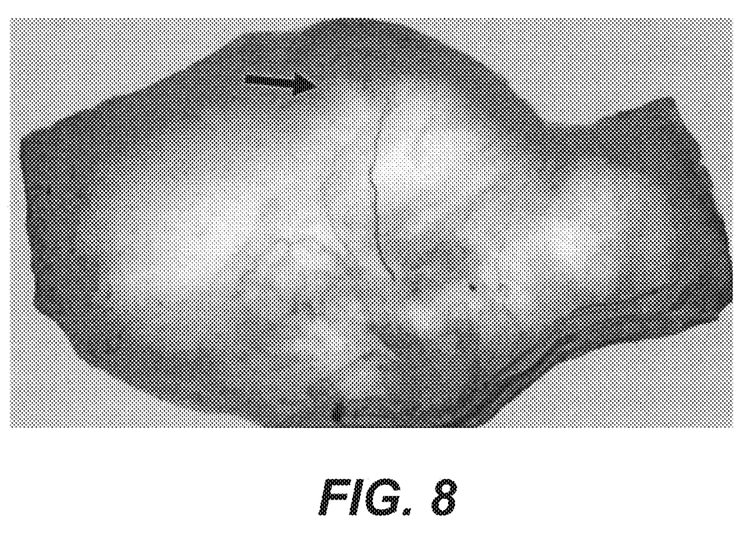
FIG. 8 shows a magnified bursa copulatrix with the ventral receptacle (arrow).
Figure 9:
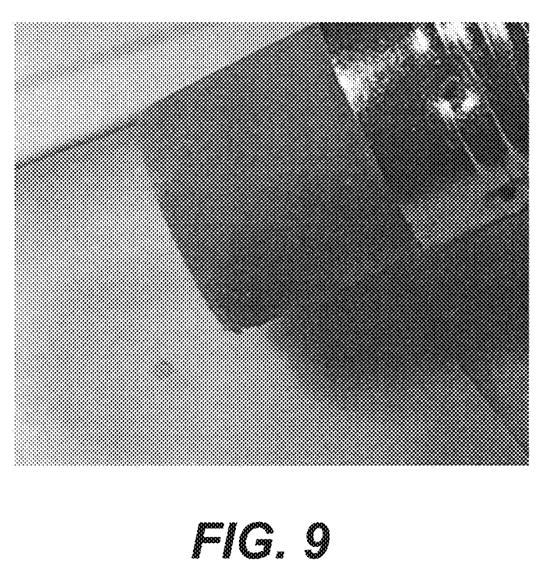
FIG. 9 shows a pencil eraser being used to apply pressure on a coverslip over the ventral receptacle, to rupture the alveoli and enable determination of whether spermatozoa are present, spilling into the lumen of the ventral receptacle if present.
Figure 10:
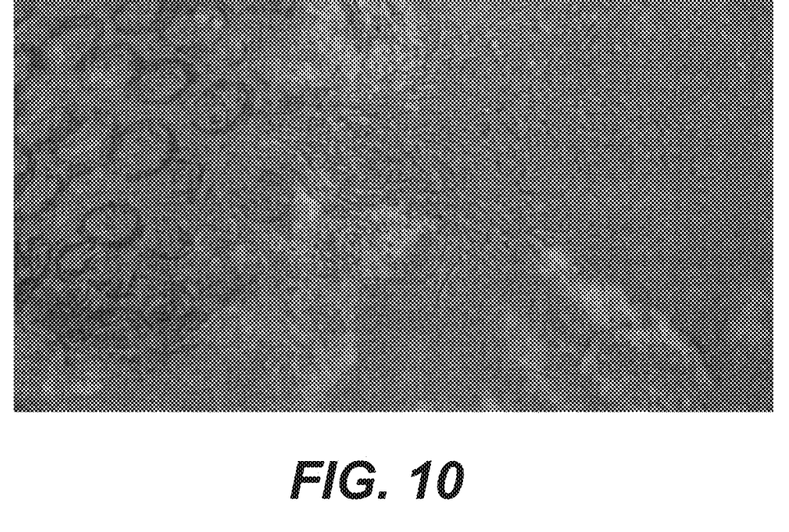
FIG. 10 shows 40× magnification using a compound microscope, showing a ruptured ventricle with spermatozoa spilling out of the rupture.

In contrast, the present methodology examines the ventral receptacle, contained in part of the bursa copulatrix. This method is depicted in FIGS. 6-10. The VR-based method generally involves cutting open the ovipositor sheath along the dorsal midline, from the base to the tip, exposing the bursa copulatrix (FIG. 6); locating and excising the portion of the bursa copulatrix that contains the ventral receptacle (FIG. 7); placing the bursa copulatrix portion, containing the ventral receptacle, on a microscope slide, and covering the portion with a slide cover-slip (FIG. 8); applying gentle, gradual pressure on the cover-slip to squeeze the bursa copulatrix/ventral receptacle, rupturing the alveoli in the ventral receptacle and spilling spermatozoa, if present, into the lumen of the ventral receptacle (FIG. 9); and examining the ruptured ventral receptacle to determine whether spermatozoa had been present in the VR, and if so, whether the spermatozoa are active (FIG. 10).

One embodiment of the present subject matter is a method for determining the mated status of female fruit flies. This method involves squashing the ventral receptacle of a female fruit fly under a microscope slide coverslip so as to rupture the alveoli in the ventral receptacle, enabling determination of whether spermatozoa had been deposited in the ventral receptacle.

Another embodiment of the present subject matter is another method for determining the mated status of female fruit flies. This method involves isolating the portion of the bursa copulatrix of a female fruit fly that contains the ventral receptacle, and applying pressure to the bursa copulatrix and ventral receptacle, so as to cause any spermatozoa stored in the seminal receptacle to be released into the lumen of the female fruit fly's ventral receptacle, enabling use of a microscope to determine whether spermatozoa had been deposited in the ventral receptacle.

Another embodiment of the present subject matter is a further method for determining the mated status of female fruit flies. This method involves exposing the bursa copulatrix of a female fruit fly by opening the posterior portion of the ovipositor sheath; excising a portion of the bursa copulatrix containing the ventral receptacle; isolating the ventral receptacle from the bursa copulatrix; and applying pressure to the ventral receptacle so as to rupture the alveoli in the ventral receptacle so as to cause spermatozoa present in the ventral receptacle to spill into the lumen of the ventral receptacle; enabling determination of whether spermatozoa had been deposited in the ventral receptacle by a male fruit fly.

THE EXAMPLES

Materials and Methods

We used the following materials and methods in practicing our new method.

Equipment

Basic Microscopy System
 a) Dissecting stereo-microscope, magnification required from 0.8× to 50×.
 b) Compound microscope, magnification from 40× to 1000× (using immersion oil).
 c) Digital camera for capturing the images.
Micro-Dissection Tools
 a) Micro-dissection scissors, Vannas style, cutting edge 2 mm.
 b) Micro-dissection forceps, straight tip, 0.025×0.005 mm.
 c) Micro-dissection forceps, 45-degree angle, serrated tip.
Microscope Slides
 a) Adhesion super frost slides, 25×75×0.1 mm.
 b) Cover glass 18×18 mm.
Stain (Optional)
 Aceto-Orcein 2% for spermathecae, and optionally for Ventral Receptacle (optional).
Immersion Oil
 a) Low viscosity immersion oil for 1000× microscopy.

Methodology

Example 1—Prior Art Spermathecal Squash Technique

Figure 1:
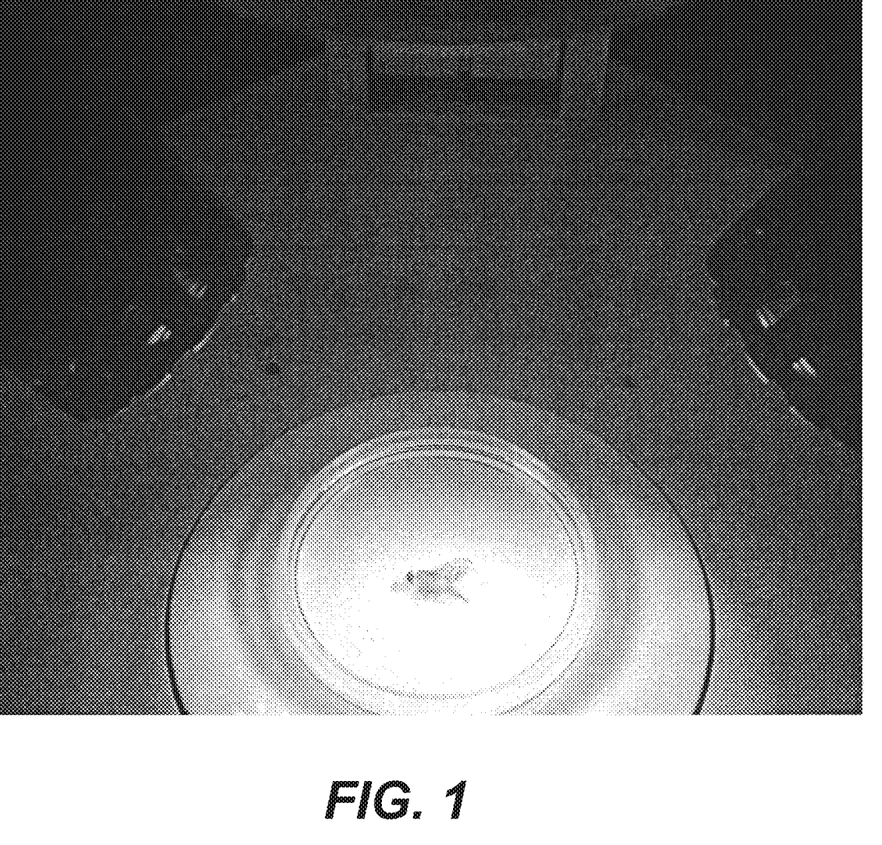
FIG. 1 shows a female fruit fly in a petri dish with sterile saline solution or Ringer's Solution, ready for visualization under a dissecting microscope.
Figure 2:
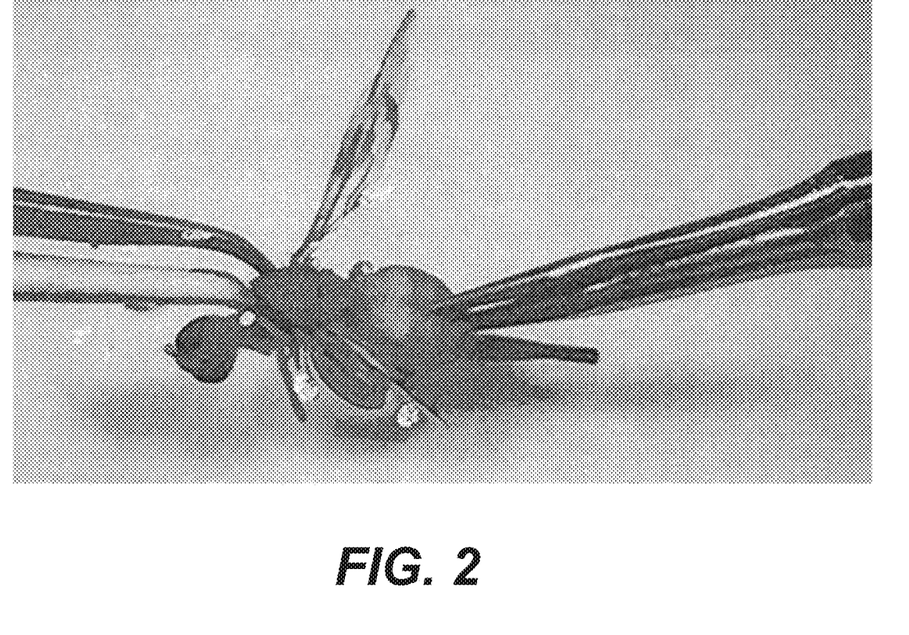
FIG. 2 shows a female fruit fly grasped by the thorax using angled forceps, with Vannas scissors being used to make an incision along the dorsal midline through the wall of the abdomen from the apex to the base.
Figure 3A:
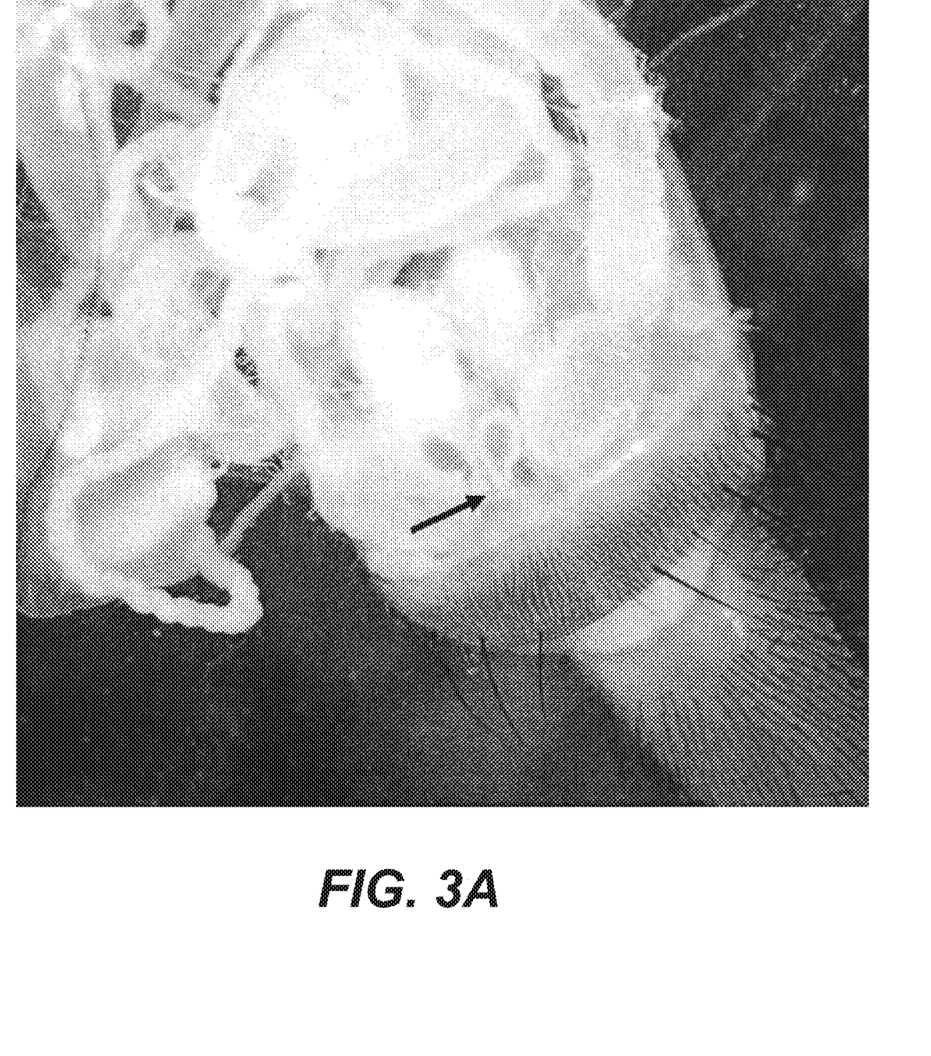
FIG. 3A shows exposed reproductive organs of the female fruit fly, ready for dissection of the spermathecae by grasping the spermathecal duct (indicated by the arrow).
Figure 3B:
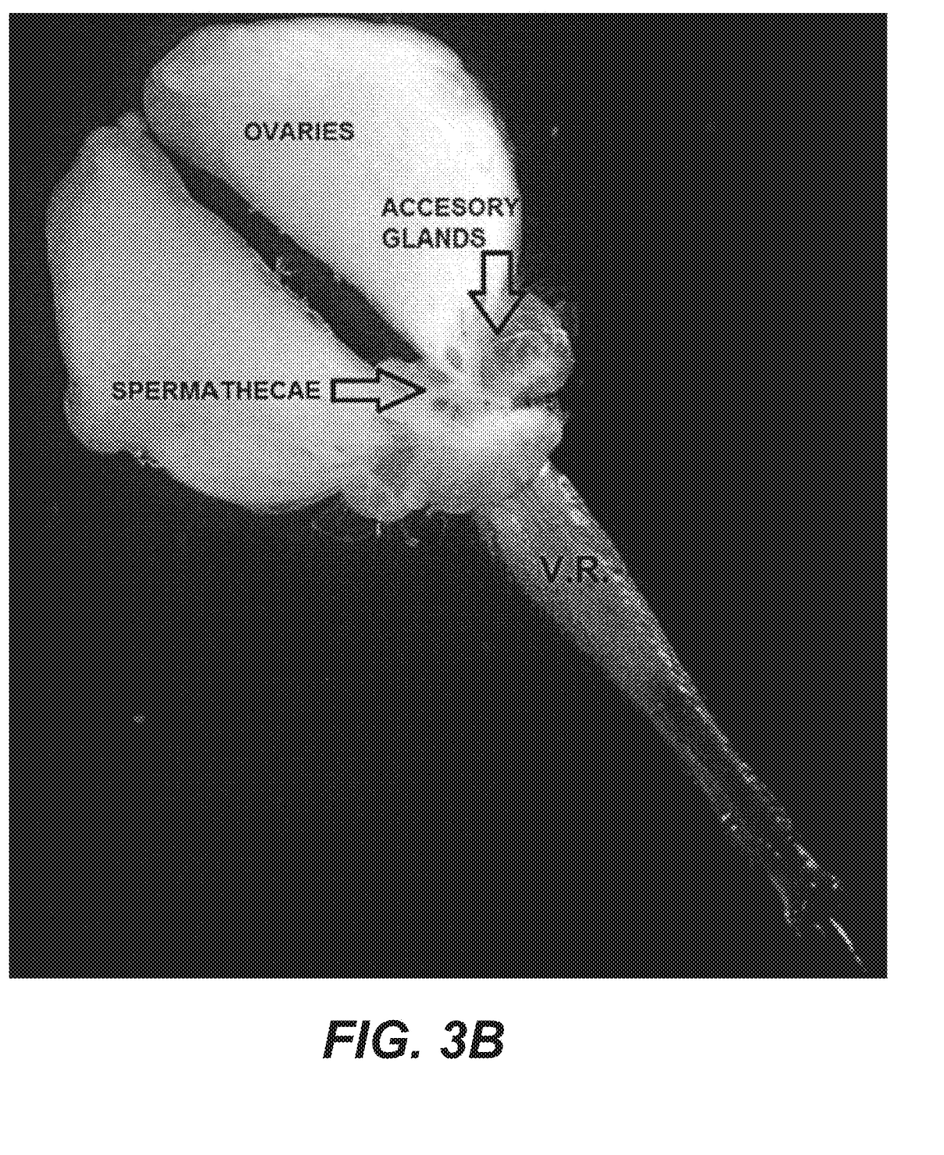
FIG. 3B shows the exposed spermathecae, in relation to the accessory glands, ovaries, and ventral receptacle (V.R.).
Figure 3C:
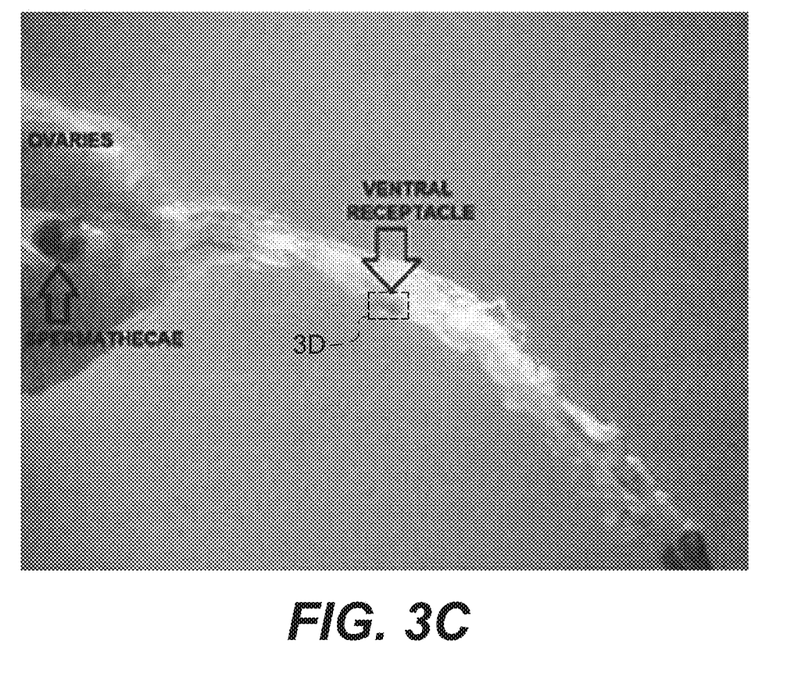
FIG. 3C shows another view of the ovaries, spermathecae, and ventral receptacle in the bursa copulatrix.
Figure 3D:
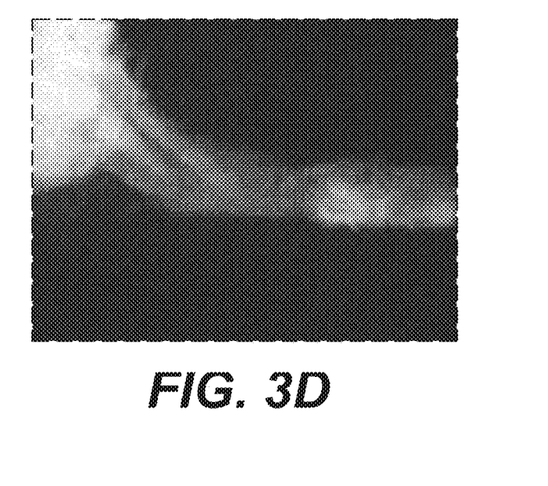
FIG. 3D shows a further magnified view of the ventral receptacle in the bursa copulatrix.

1. Place the fly in a petri dish with sterile saline solution or Ringer's Solution. Visualize the fly under the dissecting microscope. FIG. 1.
2. Grasp the fly by the thorax using the angled forceps. Use the Vannas scissors to cut open the abdomen, by making an incision along the dorsal midline through the wall of the abdomen, from the apex to the base. FIG. 2. This exposes the reproductive organs.
3. Dissect the spermathecae by using the straight-tip forceps to grasp the spermathecal duct for each spermatheca, such as is marked with an arrow in FIG. 3A, and gently pull each spermatheca away from the abdomen, removing the spermathecae from the fly. Place the spermathecae on a microscope slide, generally close to one another. FIGS. 3A, 3B, 3C, 3D.
4. Place a drop of either Aceto-Orcein stain or saline solution on the spermathecae on the slide and cover the spermathecae with a cover-slip. FIG. 4.
5. Apply gentle gradual pressure on the cover slip, such as with a pencil eraser. The pressure should be sufficient to cause a rupture of the spermathecae, so that spermatozoa present in the spermathecae is spilled from the rupture. FIG. 5. This will allow for microscopic evaluation for the presence or absence of spermatozoa, and for the activity of spermatozoa that are present.

Example 2—the New Ventral Receptacle Squash Technique

1. Again, place the fly in a petri dish with sterile saline solution or Ringer's Solution. Visualize the fly under the dissecting microscope. See FIG. 1.

Figure 6:
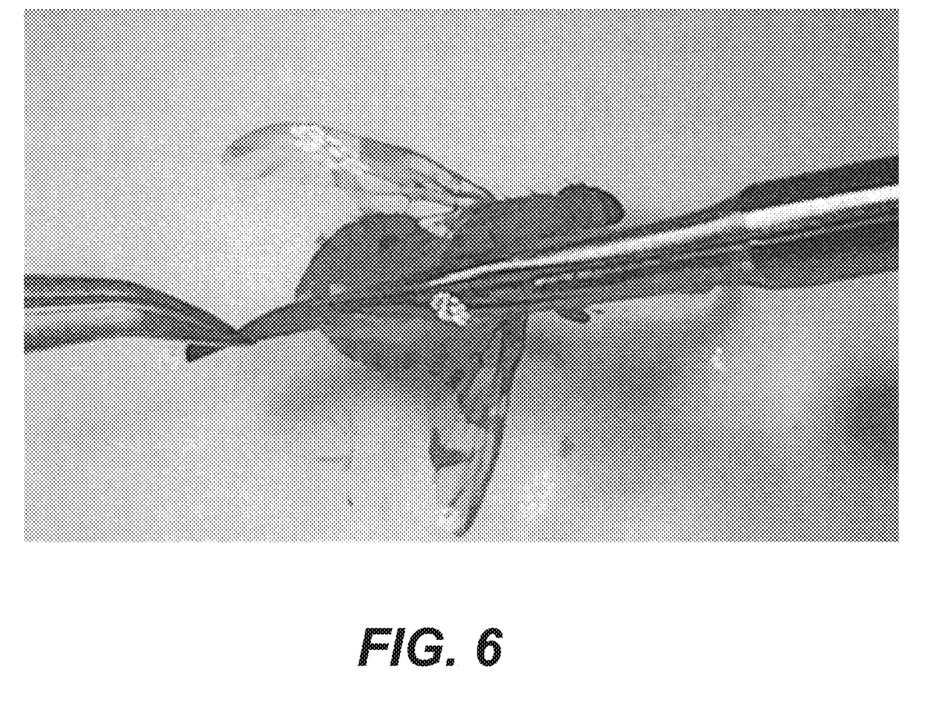
FIG. 6 shows grasping the female fruit fly by the posterior part of the ovipositor sheath using angled forceps, and using Vannas scissors to cut open the sheath along the dorsal midline from the base towards the tip, exposing the bursa copulatrix.
Figure 7:
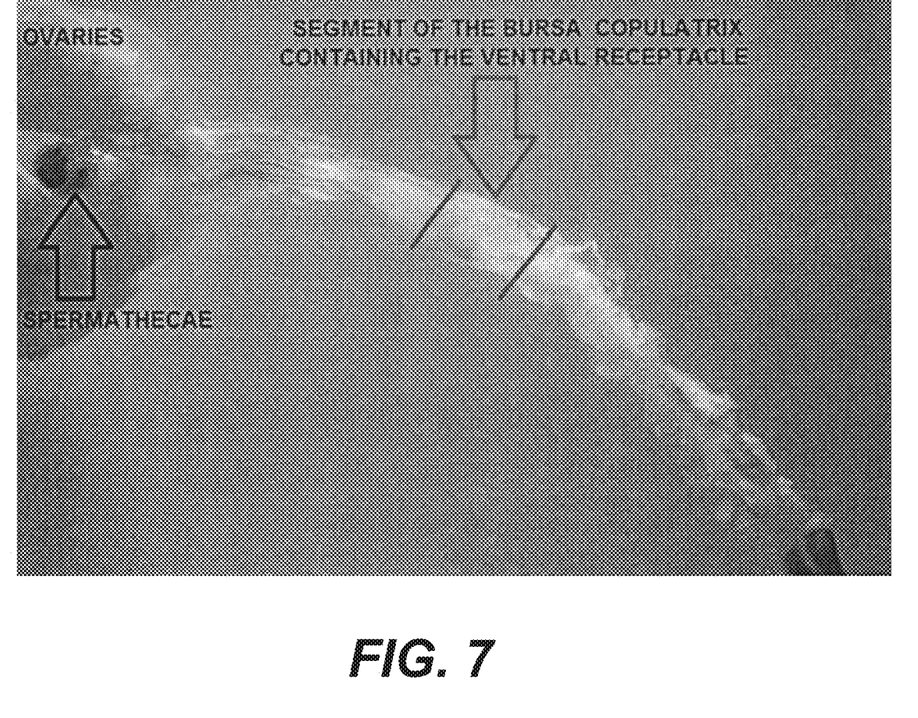
FIG. 7 shows the portion of the bursa copulatrix containing the ventral receptacle, so that incisions on either side of the ventral receptacle leaves a cylindrical segment of the bursa copulatrix containing the ventral receptacle.

2. Grasp the fly by the posterior part of the ovipositor sheath using the angled forceps. Use the Vannas scissors to open the sheath, cutting along the dorsal midline from the base towards the tip. This exposes the bursa copulatrix. FIG. 6.

3. Visualize the ventral receptacle through the wall of the bursa copulatrix, identifying the portion of the burse copulatrix that encloses the ventral receptacle. Make two complete incisions, one each about 2 mm to each side of the ventral receptacle. The cylindrical segment of the bursa copulatrix contains the ventral receptacle. See the arrow, in FIG. 7.

4. Remove the cylindrical portion of the bursa copulatrix and place the portion on a microscope slide. Moisten a coverslip by wicking it with the saline solution in the petri dish and place the coverslip on the microscope slide, covering the specimen. FIG. 8.

5. Apply gentle gradual compressing pressure on the coverslip against the slide, such as by using a pencil eraser. The pressure needs to be sufficient to gently rupture the alveoli in the ventral receptacle. FIG. 9. If spermatozoa are present in the ventral receptacle, at least some spermatozoa will be spilled from the ruptured alveoli to the lumen of the ventral receptacle.

6. Position the specimen on the slide under the compound microscope, at 40× magnification. This will enable evaluation of the presence and activity, or the absence, of spermatozoa spilled from the ruptured alveoli. The specimen may be viewed under successively increasing magnification, up to 1000× (using an oil immersion lens). Any specific magnification within the range of 40× to 1000× is contemplated as within the scope of the present subject matter, including but not limited to 50×, 60×, 70×, 80×, 90×, 100×, 200×, 300×, 400×, 500×, 600×, 700×, 800×, and 900×. Further, any contemplated range of magnifications can use any of the above as endpoints of the range. Thus, the specimen can be viewed at one magnification level, or at multiple magnification levels. FIG. 10 shows a magnified, ruptured ventral receptacle with spermatozoa having spilled from the ruptured alveoli. A live view (rather than a still photograph) may also enable evaluation of the degree of activity of any spermatozoa that are present.

It is to be understood that the new method described here is not limited to the specific embodiments described above, but instead encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of determining mated status of a female fruit fly, comprising:
   isolating a ventral receptacle or a portion of a bursa copulatrix containing the ventral receptacle from the female fruit fly;
   applying pressure to the ventral receptacle to rupture alveoli and force spermatozoa, if present, to be released from the ruptured alveoli in the ventral receptacle into a lumen of the ventral receptacle;
   detecting for the presence or absence of the spermatozoa in the lumen of the ventral receptacle; and
   determining that the female fruit fly has a positive mated status when the presence of the spermatozoa is detected.

2. The method of claim 1, comprising the steps of:
   (a) cutting open an ovipositor sheath of the female fruit fly along a dorsal midline to expose the bursa copulatrix;
   (b) locating the ventral receptacle within the portion of the bursa copulatrix containing the ventral receptacle;
   (c) removing from the female fruit fly the portion of the bursa copulatrix containing the ventral receptacle; and
   (d) magnifying the lumen of the ventral receptacle to evaluate whether the spermatozoa are present or absent, wherein the step of applying the pressure to the ventral receptacle comprises applying pressure to the portion of the bursa copulatrix containing the ventral receptacle, the pressure rupturing the alveoli in the ventral receptacle to cause the spermatozoa, if present, to be released in to the lumen.

3. The method of claim 1, wherein the isolated ventral receptacle is no longer contained in the bursa copulatrix or portion thereof.

4. The method of claim 2, wherein the female fruit fly's ovipositor sheath is cut open using Vannas scissors and angled forceps.

5. The method of claim 2, wherein the bursa copulatrix is removed from the female fruit fly after being incised on both sides of the ventral receptacle contained in the bursa copulatrix.

6. The method of claim 1, wherein the isolated ventral receptacle is removed from the portion of bursa copulatrix, the portion of bursa copulatrix being incised and removed from the female fruit fly.

7. The method of claim 2, wherein the portion of the bursa copulatrix removed in step (c) is placed on a microscope slide before the pressure is applied.

8. The method of claim 7, wherein the portion of the bursa copulatrix placed on the microscope slide is then covered by a slide coverslip before the pressure is applied.

9. The method of claim 8, wherein the pressure is applied to the slide coverslip, squeezing the bursa copulatrix portion against the microscope slide.

10. The method of claim 4, wherein step (a) further comprises grasping the female fruit fly's ovipositor sheath using angled forceps before cutting open the ovipositor sheath using Vannas scissors.

11. The method of claim 10, wherein before step (c), the portion of the bursa copulatrix containing the ventral receptacle is incised on both sides of the ventral receptacle contained in the bursa copulatrix.

12. The method of claim 11, wherein the portion of the bursa copulatrix containing the ventral receptacle is placed on a microscope slide before the pressure is applied.

13. The method of claim 12, wherein the portion of the bursa copulatrix placed on the microscope slide is then covered by a slide coverslip before the pressure is applied.

14. The method of claim 13, wherein the pressure is applied to the slide coverslip, squeezing the bursa copulatrix portion between the slide coverslip and the microscope slide.

15. The method of claim 14, wherein the magnification in step (d) includes at least one magnification between 40× and 1000×.

16. The method of claim 15, wherein the magnification in step (d) is completed at multiple magnification levels.

17. The method of claim 1, wherein the method further comprises visually evaluating an activity level of spermatozoa that are present with a microscope.

18. The method of claim 15, wherein the method further comprises visually evaluating an activity level of spermatozoa that are present with a microscope.

19. The method of claim 16, wherein the method further comprises visually evaluating an activity level of spermatozoa that are present with a microscope.

* * * * *